United States Patent [19]

Polanek et al.

[11] Patent Number: 5,227,553

[45] Date of Patent: Jul. 13, 1993

[54] SELECTIVE HYDROGENATION OF CRUDE HIGH-BUTADIENE C4 CUTS

[75] Inventors: Peter Polanek, Weinheim; Dietmar Posselt, Ludwigshafen; Peter Schreyer, Weinheim, all of Fed. Rep. of Germany

[73] Assignee: BAST Aktiengesellschaft, Ludwigshafen, Fed. Rep. of Germany

[21] Appl. No.: 887,038

[22] Filed: May 22, 1992

[51] Int. Cl.$^5$ ................................................ C07C 5/05
[52] U.S. Cl. .................................... 585/259; 585/265; 585/271; 585/841
[58] Field of Search ................ 585/259, 265, 841, 271

[56] References Cited

U.S. PATENT DOCUMENTS

| | | | |
|---|---|---|---|
| 2,402,493 | 6/1946 | Greensfelder | 585/259 |
| 3,113,983 | 12/1963 | Kirsch et al. | 585/259 |
| 3,655,799 | 4/1972 | Lassau et al. | 585/265 |
| 3,770,619 | 11/1973 | Derrien et al. | 585/258 |
| 5,059,731 | 10/1991 | Berrebi | 585/259 |

OTHER PUBLICATIONS

R. F. Peterson "Hydrogenation Catalysts, Noyer Data Corporation", N.Y. 1977 p. 183.
G. C. Bond "Catalysis by Metals" Academy Press London 1962 pp. 99 & 297.

*Primary Examiner*—Anthony McFarlane
*Attorney, Agent, or Firm*—Keil & Weinkauf

[57] ABSTRACT

A process for the selective hydrogenation of butadiene to butenes in the liquid phase or trickle phase in contact with a fixed-bed supported noble metal catalyst, wherein a high-butadiene $C_4$ stream having a butadiene content of from 20 to 80% w/w, based on the weight of the $C_4$ stream, is hydrogenated in a cascade of two reaction zones such that the hydrogenation product from the first reaction zone has a butadiene content of from 0.1 to 20% w/w and the hydrogenation product from the second reaction zone has a butadiene content of from 0.005 to 1% w/w, based in both cases on the weight of the $C_4$ stream, provided that the butadiene content of the hydrogenation product from the second reaction zone is at least 5 times smaller than that of the hydrogenation product from the first reaction zone.

7 Claims, No Drawings

SELECTIVE HYDROGENATION OF CRUDE HIGH-BUTADIENE C4 CUTS

BACKGROUND OF THE INVENTION

1. Field of the Invention

The invention relates to a process for the selective hydrogenation of butadiene in crude high-butadiene $C_4$ cuts to butenes. Such $C_4$ hydrocarbon mixtures mainly occur when hydrocarbons originating from mineral oils, for example naphtha, are steam cracked. These hydrocarbon mixtures can contain, in addition to the chief component 1,3-butadiene, small amounts of compounds containing cumulenes and/or acetylenic triple bonds, which can also be selectively hydrogenated to butenes in the present process.

The composition of the crude $C_4$ cut coming from the steam cracker can vary within wide limits (cf Table 1 below).

TABLE 1

Two typical examples of the composition of $C_4$ cuts leaving a steam cracker in percentages by weight

|  | I | II |
| --- | --- | --- |
| Butadiene | 46 | 63 |
| Butene-1 | 13 | 9 |
| trans-Butene-2 | 4 | 3 |
| cis-Butene-2 | 3 | 2 |
| Isobutene | 24 | 20 |
| Isobutane | 3 | 0.5 |
| n-Butane | 6 | 2 |
| Vinylacetylene | 1 | 0.5 |

The composition is substantially dependent on that of the product to be cracked and on the cracking conditions in the steam cracker. The resulting crude $C_4$ cut usually has a butadiene content of from 40 to 50% w/w.

Indeed, the process of the invention is capable of selectively hydrogenating any $C_4$ cut having a butadiene content of up to 80% w/w, regardless of its origin.

2. Description of the Prior Art

Hitherto, such crude $C_4$ cuts have been processed by methods involving the extraction of the butadiene with suitable solvents. Such methods are described in detail in, say, DE 2,724,365 and have been adopted for the operation of numerous industrial plants. The butadiene thus isolated can be used, for example, for making styrene-butadiene copolymers suitable, inter alia, for packaging foodstuffs.

In cases in which the separation of butadiene would be uneconomical, there is the alternative of selectively hydrogenating the butadiene to butenes. The latter form valuable products which can be processed to higher value-added chemicals.

Possible routes for such further processing of butenes are, for example:
- conversion of isobutene to methyl-tert-butyl ether or tert-butylalcohol
- isolation of isobutene to serve as intermediate for polyisobutene or other products
- isolation of butene-1, for example by fractional distillation
- dimerization of n-butenes to octenes with subsequent conversion to plasticizer alcohols A basic prerequisite for the above upgrading processes, given by way of example, is the use of a virtually butadiene-free product having a maximum butadiene content of ca 0.2% w/w, as otherwise the formation of by-products in the form of undesirable oligomers and polymers will be too great.

Another use is, e.g., the copolymerization of ethylene and butene-1 to give so-called linear low-pressure and high-pressure polyethylenes, which are manufactured in large quantities on account of their improved application properties as compared with normal polyethylenes.

Such butadiene-free $C_4$ cuts have hitherto been obtained only by the method of butadiene extraction, which reduces the butadiene content to about 1% w/w.

One conventional method of removing residual butadiene from butene-enriched $C_4$ mixtures comprises selective catalytic hydrogenation. For example, DE 3,301,169 describes a process for the preparation of butadiene-free or virtually butadiene-free butene-1 from $C_4$ streams having a butadiene content of up to 5% w/w by selective hydrogenation of the butadiene. The addition of small amounts of CO results in a selectivity of virtually 100%, even when hydrogenation is carried to very low residual butadiene contents of 10 ppm. This measure also greatly inhibits or prevents the isomerization of butene-1 to butene-2.

The selective hydrogenation of residual butadiene using added CO can be carried out by conventional methods in, e.g., the gas phase, liquid phase, or trickle phase. It is preferred to effect such selective hydrogenation of residual butadiene in the liquid phase or trickle phase using a fixed bed of hydrogenation catalyst.

EP 0,087,980 describes a method of carrying out the reaction in the gas phase, in which the hydrogen is fed to the reactor at at least two points.

DE 3,143,647 discloses a process for the selective hydrogenation of $C_3$ and $C_4$ hydrocarbons containing conjugated and cumulated double bonds and/or acetylenic triple bonds, by the use of fixed-bed supported catalysts, in which a) a finely distributed stream of hydrogen is homogeneously dissolved in the hydrocarbon to be hydrogenated before the latter enters the reactor, and b) at least 0.05 ppm w/w of CO must be added. This method makes it possible to hydrogenate butadiene-containing cuts having butadiene contents of up to 20% w/w.

Such hydrogenations can be carried out using conventional fixed-bed catalysts. Particularly suitable catalysts are metals in Subgroup VIII and Subgroup I of the periodic table, supported, for example, on aluminum oxide, pumice, clays, or silicates. $TiO_2$ has also been proposed for use as a supporting material, cf EP 0,314,020.

Suitable catalysts, mainly for use in the selective hydrogenation of butadiene, pentadiene, and cyclopentadiene, are disclosed, e.g., in DE-A 3,207,029, DE-A 3,207,030, DE-A 3,143,647, and EP-A 0,011,906. These are supported palladium catalysts, the supports mainly being $Al_2O_3$ or $SiO_2$.

A significant improvement in the selectivity achieved in diene and acetylene hydrogenations can be obtained by partial poisoning, for example by adding promoters (Zn, Cd, Sn, Pb, or Hg) to the Pd-catalysts (cf G. C. Bond, *Catalysis by Metals*, Academic Press, London 1962, pp 99 and 297). More recently proposed promoters are, e.g., Ag (DE 3,119,850) and catalysts pretreated with inorganic bases (DE 2,849,026) or doped with alkali metal oxides or alkaline-earth metal oxides (R. J. Peterson, Hydrogenation Catalysts, Noyes Data Corp., New York 1977, p 183).

Besides the aforementioned addition of CO as a means of increasing the selectivity, it has also been proposed to modify catalysts with sulfur compounds. Thus it is possible to treat catalysts with thioethers to increase their selectivity toward acetylene, as proposed in FR 1,240,175. Finally, FR 2,355,792 discloses catalysts doped with hydrogen sulfide which are suitable for the selective hydrogenation of butadiene. However, they also catalyze the isomerization of, e.g., butene-1 to butene-2.

The aforementioned processes are unsatisfactory due to the facts that they are restricted to the use of products having low butadiene contents and/or that they require the addition of CO to increase the selectivity.

The use of compounds such as CO for increasing the selectivity is a disadvantage in the hydrogenation of high-butadiene streams since it necessitates the use of much higher reaction temperatures in order to achieve the desired conversions. However, high temperatures increase the occurrence of side-reactions (oligomerization, polymerization, overreaction to butane) and reduce the lifetime of the catalysts.

SUMMARY OF THE INVENTION

It is thus an object of the present invention to provide a process for the selective hydrogenation of high-butadiene $C_4$ cuts which
can be run using fixed-bed catalysts,
causes the compounds to be hydrogenated to convert to simple compounds which remain so as far as possible, and
can be operated without the addition of CO.

DESCRIPTION OF THE PREFERRED EMBODIMENTS

According to the present invention, this object is achieved with a process for the selective hydrogenation of butadiene to butenes in the trickle phase in contact with a fixed-bed supported catalyst, wherein a high-butadiene $C_4$ stream having a butadiene content of from 20 to 80% w/w, based on the weight of the $C_4$ stream, is hydrogenated in a cascade of two reaction zones such that the hydrogenation product from the first reaction zone has a butadiene content of from 0.1 to 20% w/w and the hydrogenation product from the second reaction zone has a butadiene content of from 0.005 to 1% w/w, based in both cases on the weight of the $C_4$ stream, provided that the butadiene content of the hydrogenation product from the second reaction zone is at least 5 times smaller than that of the hydrogenation product from the first reaction zone.

According to a preferred embodiment, the butadiene content of the hydrogenation product from the second reaction zone is at least 10 times smaller, and more preferably at least 20 times smaller, than that of the hydrogenation product from the first reaction zone.

A wide variety of butadiene-containing $C_4$ streams can be used in the process of the invention. It is preferred to use $C_4$ cuts containing from 30 to 60% w/w of butadiene. Other possible constituents of such cuts are vinylacetylene, butyne-1, butyne-2, butene-1, butene-2, isobutene, n-butane and/or isobutane. Vinylacetylene and butynes are also selectively hydrogenated to butenes, whilst isobutene, n-butane, and isobutane leave the process of the invention unchanged.

The process of the invention is advantageously carried out in the liquid phase or trickle phase, and the hydrogen is finely distributed in the liquid $C_4$ stream in conventional manner. We prefer to carry out our selective hydrogenation of butadiene in the trickle phase using a fixed-bed hydrogenation catalyst.

Suitable hydrogenation catalysts are supported noble metal catalysts containing palladium, platinum, silver, gold, rhodium, ruthenium, osmium, or mixtures of such metals. Particularly preferred catalysts are supported catalysts containing palladium.

The two reaction zones must be sufficiently far apart to enable hydrogen to be introduced and finely distributed at a point between them. Preferably, the two reaction zones are in the form of discrete hydrogenation reactors. The hydrogen is added in an amount which is equal to the stoichiometric amount for theoretical conversion or is up to twice the stoichiometric amount. Preferably, the amount added is equal to the stoichiometric amount or forms a hydrogen excess of up to 1.2 times the stoichiometric amount.

The hydrogen used for the hydrogenation may contain up to 30% molar of inert gas such as methane without being detrimental to the hydrogenation. The hydrogen used for the process of the invention is preferably free from CO, but small amounts of CO have no adverse effects.

The reaction conditions in each of the two reaction zones may be varied within wide limits. Thus the process of the invention operates at reaction temperatures ranging from 20° to 200° C., preferably from 40° to 120° C., and under pressures ranging from 5 to 50 bar, preferably from 5 to 30 bar, and at a liquid hourly space velocity (lhsv) of from 0.1 to 30 $h^{-1}$, preferably from 1 to 10 $h^{-1}$.

The process of the invention has a number of advantages. The butadiene contained in the charge is hydrogenated virtually quantitatively and with a very high degree of selectivity. Despite the very high butadiene concentration, the butene selectivity S achieved is at least 96%.

$$S_{butene} = \frac{\text{Amount of butadiene converted to butenes}}{\text{Total amount of butadiene converted}} \times 100$$

The hydrogenation is selective over a very wide range extending to extremely high butadiene contents. Isomerization of butene-1 to butene-2 is only slight, and isobutene is not converted to isobutane. The hydrogen need not comply with any special purity specifications provided it contains no irreversible catalyst poisons such as lead or arsenic. Metering of the hydrogen is easy to control by means of automatic analysis methods.

The selectivity is not reduced when higher reaction temperatures occur, so that there is no need for cooling means or refrigerating plants. Heat removal is simply controlled by recycling a sufficient amount of liquid from the hydrogenated product.

Furthermore, no appreciable amounts of oligomerization products are formed in the process of the invention.

The invention is illustrated by, but not limited to, the following examples.

EXAMPLE 1

Hydrogenation of a $C_4$ cut having the composition given in Table 2 below was carried out in two fixed-bed reactors arranged as a cascade. Each of the reactors was provided with a separator and means for circulating the liquid. The rates of flow of the recycled liquid and the off-gas could be varied within wide limits. The reactions were carried out by trickling the $C_4$ cut over a supported catalyst containing 0.5% w/w of palladium.

The gas used for hydrogenation was composed of 90% v/v of hydrogen and 10% v/v of methane and was metered to the reactors at rates appropriate to the butadiene content of the C$_4$ cut entering them. Means for removing samples were provided downstream of each reactor. The liquid hourly space velocity of the C$_4$ cut was 8.8 L/(L·h). The first stage of the hydrogenation was carried out at a reactor inlet temperature of 53° C. and a reactor pressure of 14.1 bar.

The second stage of the hydrogenation took place at a reactor inlet temperature of 63° C. and a total pressure in the reactor of 9.5 bar.

The overall two-stage hydrogenation reduced the butadiene content from 46.1% w/w to 0.2% w/w, and the selectivity toward butenes was 97.6%.

The compositions of the products are listed in Table 2 below in percentages by weight.

TABLE 2

|  | C$_4$ MIXTURE treated | HYDROGENATION PRODUCT leaving | |
|---|---|---|---|
|  |  | 1st Stage | 2nd Stage |
| Butadiene | 46.1 | 5.8 | 0.2 |
| Butene-1 | 11.5 | 35.8 | 32.6 |
| trans-Butene-2 | 3.8 | 17.9 | 25.0 |
| cis-Butene-2 | 2.6 | 3.8 | 5.1 |
| Isobutene | 23.9 | 23.9 | 23.9 |
| Isobutane | 4.3 | 4.3 | 4.3 |
| n-Butane | 7.8 | 8.5 | 8.9 |

EXAMPLE 2

Comparative Example

Using a single hydrogenation zone containing the same catalyst as in Example 1, the same C$_4$ cut was tricled over the catalyst to attain a final butadiene content of 0.3% w/w. The composition of the hydrogenating gas was also the same.

The reaction was carried out at a liquid hourly space velocity of the C$_4$ cut of 5.4 L/(L·h), and the reactor inlet temperature was 67° C., the total pressure in the reactor 19.8 bar.

The selectivity toward butene in this single-stage hydrogenation of a high-butadiene C$_4$ cut was only 71.4%.

The results of this test are shown by Table 3 below, in which the contents of the components are given as percentages by weight.

TABLE 3

|  | C$_4$ MIXTURE treated | HYDROGENATION PRODUCT obtained by single-stage method |
|---|---|---|
| Butadiene | 46.1 | 0.3 |
| Butene-1 | 11.5 | 8.0 |
| trans-Butene-2 | 3.8 | 28.8 |
| cis-Butene-2 | 2.6 | 13.8 |
| Isobutene | 23.9 | 23.9 |
| Isobutane | 4.3 | 4.3 |
| n-Butane | 7.8 | 20.9 |

EXAMPLE 3

Using the same experimental setup as described in Example 1, a high-butadiene C$_4$ cut having the composition given in Table 4 below was selectively hydrogenated in two stages. The same supported palladium catalyst was used, and the hydrogenating gas was composed of 90% v/v of hydrogen and 10% v/v of methane. The liquid hourly space velocity of the C$_4$ cut used was 6.0 L/(L·h).

The first stage of the hydrogenation was carried out at a reactor inlet temperature of 55° C. and a reactor pressure of 20.2 bar, and the second stage took place at a reactor inlet temperature of 66° C. and a reactor pressure of 10.4 bar.

The overall two-stage hydrogenation reduced the butadiene content from 71.1% w/w to 0.05% w/w, and the overall selectivity toward butenes was 97.0%.

The contents of the components of the various products are listed in percentages by weight in Table 4 below.

TABLE 4

|  | C$_4$ MIXTURE treated | HYDROGENATION PRODUCT leaving | |
|---|---|---|---|
|  |  | 1st Stage | 2nd Stage |
| Butadiene | 71.1 | 4.1 | 0.05 |
| Butene-1 | 7.3 | 38.4 | 32.5 |
| trans-Butene-2 | 2.9 | 29.7 | 30.7 |
| cis-Butene-2 | 1.8 | 9.5 | 17.7 |
| Isobutene | 15.0 | 15.0 | 15.0 |
| Isobutane | 0.4 | 0.4 | 0.4 |
| n-Butane | 1.5 | 2.9 | 3.6 |

We claim:

1. A process for the selective hydrogenation of 1,3-butadiene to butenes in the liquid phase or trickle phase in contact with a fixed-bed supported noble metal catalyst, wherein a C$_4$ stream having a 1,3-butadiene content of from 20 to 80% w/w, based on the weight of the C$_4$ stream, is hydrogenated in a cascade of two reaction zones wherein each of the two reaction zones is operated at reaction temperatures ranging from 40° C. to 120° C., pressures ranging from 5 to 50 bar wherein the pressure in the second reaction zone is lower than the pressure in the first reaction zone, and liquid hourly space velocities of the C$_4$ stream ranging from 0.1 to 30 h$^{-1}$, such that the hydrogenation product from the first reaction zone has a 1,3-butadiene content of from 0.1 to 20% w/w and the hydrogenation product from the second reaction zone has a 1,3-butadiene content of from 0.005 to 1% w/w, based in both cases on the weight of the C$_4$ stream, wherein the 1,3-butadiene content of the hydrogenation product from the second reaction zone is at least 5 times smaller than that of the hydrogenation product from the first reaction zone, and wherein the selectivity achieved for the conversion of 1,3-butadiene in the direction of butenes is at least 96%.

2. A process as claimed in claim 1, wherein the two reaction zones are in the form of two separate hydrogenation reactors.

3. A process as claimed in claim 1, wherein the hydrogen is fed to each of the reaction zones in an amount equal to the stoichiometric amount or exceeding the latter by up to 100%.

4. A process as claimed in claim 1, wherein the residual butadiene content of the stream leaving the first reaction zone is adjusted to from 0.1 to 10% w/w.

5. A process as claimed in claim 1, wherein the catalyst used is palladium on an inert support.

6. A process as claimed in claim 1, wherein hydrogenation is carried out using a gas containing hydrogen and up to 30% molar of inert gases.

7. A process as defined in claim 2, wherein the hydrogen is fed to each of the reaction zones in an amount equal to the stoichiometric amount or exceeding the letter by up to 100%.

* * * * *